United States Patent
Vollmann et al.

(10) Patent No.: US 10,407,341 B2
(45) Date of Patent: Sep. 10, 2019

(54) LITHIUM SILICATE GLASS CERAMIC

(71) Applicant: DENTSPLY SIRONA Inc., York, PA (US)

(72) Inventors: Markus Vollmann, Gelnhausen (DE); Irmgard Wissel, Freigericht (DE); Marcel Meegdes, Russelsheim (DE); Carsten Wiesner, Rockenberg (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/717,565

(22) Filed: Sep. 27, 2017

(65) Prior Publication Data

US 2018/0099900 A1    Apr. 12, 2018

(30) Foreign Application Priority Data

Oct. 7, 2016 (DE) .................... 10 2016 119 108

(51) Int. Cl.

| | | |
|---|---|---|
| *C03C 10/00* | (2006.01) | |
| *A61C 13/00* | (2006.01) | |
| *C03B 32/02* | (2006.01) | |
| *C03C 4/00* | (2006.01) | |
| *C03C 3/097* | (2006.01) | |

(52) U.S. Cl.
CPC ...... *C03C 10/0027* (2013.01); *A61C 13/0022* (2013.01); *C03B 32/02* (2013.01); *C03C 3/097* (2013.01); *C03C 4/0021* (2013.01); *C03C 2204/00* (2013.01)

(58) Field of Classification Search
CPC . C03B 25/02; C03C 10/0009; C03C 10/0027; C03C 3/097; C03C 4/0021; C03C 4/20; C03C 4/02; A61K 6/0235; A61K 6/024; A61K 6/025; A61K 6/0273
See application file for complete search history.

(56) References Cited

U.S. PATENT DOCUMENTS

| | | | |
|---|---|---|---|
| 4,515,634 A | 5/1985 | Wu | |
| 2014/0141960 A1* | 5/2014 | Borczuch-Laczka | ........................ A61K 6/0235 501/32 |
| 2015/0274581 A1 | 10/2015 | Beall | |
| 2016/0229742 A1* | 8/2016 | Wondraczek | ........... C03B 25/02 |

FOREIGN PATENT DOCUMENTS

| | | |
|---|---|---|
| DE | 19750794 A1 | 6/1999 |
| DE | 102007011337 A1 | 9/2008 |
| DE | 102009060274 A1 | 6/2011 |

(Continued)

OTHER PUBLICATIONS

International Search Report, PCT/EP2017/074692, Dec. 13, 2017 (completed), dated Dec. 21, 2017.

(Continued)

*Primary Examiner* — Noah S Wiese
(74) *Attorney, Agent, or Firm* — Dentsply Sirona Inc.

(57) ABSTRACT

The invention relates to a lithium silicate glass ceramic, which contains at least lithium disilicate as a crystal phase, and lithium aluminum silicate as further crystal phase. The lithium silicate glass ceramic in its initial composition contains $Al_2O_3$ at 1.5 to 3.5 percent by weight, and $K_2O$ at 0.6 to 1.8 percent by weight.

12 Claims, 4 Drawing Sheets

(56) References Cited

FOREIGN PATENT DOCUMENTS

| | | |
|---|---|---|
| DE | 10336913 B4 | 1/2014 |
| EP | 0231773 A1 | 8/1987 |
| EP | 1484031 B1 | 8/2007 |
| EP | 2662342 A1 | 11/2013 |
| EP | 3059214 A1 | 8/2016 |
| WO | 2012175450 A1 | 12/2012 |
| WO | 2012175615 A1 | 12/2012 |
| WO | 2013053865 A2 | 4/2013 |
| WO | 20170670909 A1 | 4/2017 |

OTHER PUBLICATIONS

"Characterisation and Properties of Lithium Disilicate Glass Ceramics in the Si02-LI20-K20-A1203System for Dental Applications"; Advances in Materials Science and Engineering; Jan. 1, 2013; pp. 1-11.
Written Opinion of the International Searching Authority; PCT/EP2017/074692; dated Dec. 21, 2017.

\* cited by examiner

LITHIUM SILICATE GLASS CERAMIC

TECHNICAL FIELD

The invention relates to a lithium silicate glass ceramic, intended for a dental form body, containing lithium disilicate and lithium aluminum silicate as crystal phases.

The invention also relates to a method for the production of a lithium silicate glass ceramic intended for a dental form body.

The subject of the invention is further the use of a lithium silicate glass ceramic.

BACKGROUND OF THE INVENTION

The use of lithium silicate glass ceramic has been proven in the field of dental technology because of its strength and biocompatibility. The strength can additionally be increased through the addition of a stabilizer from the group zirconium oxide, hafnium oxide, or mixtures thereof, to the starting substances (DE 10 2009 060 274 A1, WO 2012/175450 A1, WO 2012/175615 A1, WO 2013/053865 A2, EP 2 662 342 A1).

Lithium silicate glass ceramic materials, in particular when a blank contains lithium metasilicate as the main crystal phase, enable machine working without difficulty, without substantial wear of the tool. To increase strength heat treatment is then applied to convert the lithium metasilicate at least in part into lithium disilicate (DE 197 50 794 A1, DE 103 36 913 B4).

To manufacture dentures it is known to press plasticized ceramic material in a mold cavity present in a curable embedding mass (EP 1 484 031 B1, EP 0 231 773 A1).

DE 10 2007 011 337 A1 relates to veneer ceramics for dental restorations in which frame work ceramic is made of yttrium-stabilized zirconium dioxide. The main crystal phase of the ceramic comprises lithium disilicate. Lithium aluminum silicate is added.

US 2015/0274581 A1 relates to glass ceramic compositions having a combination of lithium disilicate and spodumene as crystalline phases.

A lithium silicate crystallized glass according to EP 3 059 214 A1 contains lithium metasilicate, lithium disilicate, lithium phosphate, cristobalite, tridymite, quartz, or spodumene.

When using lithium silicate glass ceramic sometimes the disadvantage is given, that the components influencing the strength could crystallize with the result, that the aesthetic is affected.

SUMMARY OF THE INVENTION

Object of the present invention is to make a lithium silicate glass ceramic available together with a method to produce it, which, inter alia, is characterized by a high strength without showing drawbacks in respect to its aesthetic appearance.

To achieve the object of the invention, among other things the lithium silicate glass ceramic intended for a dental molded body is characterized in that the lithium silicate glass ceramic in its initial composition contains $Al_2O_3$ at 1.5 to 3.5 percent by weight, and $K_2O$ at 0.6 to 1.8 percent by weight.

It was surprisingly found that when the lithium silicate glass ceramic contains as a further crystal phase crystals/crystallites of lithium aluminum silicate, in particular spodumene, not only the strength can be substantially increased, but simultaneously due to the narrowly prescribed percentage by weight of $K_2O$ (0.6 wt % to 1.8 wt %) and $Al_2O_3$ (1.5 wt % to 3.5 wt %) firstly the stabilizers as zirconium oxide present is dissolved in the glass phase and secondly a discoloration respectively opacity is avoided. The value ranges in this respect characterize the invention independently of further selected parameters or components and their concentrations.

The invention is in particular characterized in that the lithium silicate glass ceramic contains spodumene (LiAl[$Si_2O_6$]) in a percentage by volume (vol %) of the lithium silicate glass ceramic that is above 0 to 10 vol %, in particular more than 0 vol % to 5 vol %, especially preferred more than 0 vol % to 2 vol %, more especially preferred more than 0 vol % to 1 vol %, virgilite ($Li_xAl_xSi_{3-x}O_6$) in a percentage by volume 0 vol % to 5 vol %, in particular 0 vol % to 2 vol %, especially preferred 0 vol % to 1 vol %, of the glass ceramic.

Possibly the small amount of spodumene is the reason for a further increase of strength.

It is further of advantage if the lithium silicate glass ceramic contains sogdianite ($Zr_2KLi_3(Si_{12}O_{30})$) which leads to an increase in strength through surface crystallization. The sogdianite may be contained in the range 0 vol % to 20 vol % of the glass ceramic.

The lithium silicate glass ceramic is in particular characterized in that the glass ceramic in addition to lithium aluminum silicate or lithium aluminum silicates also contains lithium phosphate and lithium disilicate as crystal phases, preferably in addition to lithium aluminum silicate or lithium aluminum silicates, exclusively lithium phosphate and lithium disilicate as crystal phases.

The lithium silicate glass ceramic is further characterized in that the percentage by volume of the crystal phases lithium disilicate and lithium phosphate is in the range 40 vol % to 60 vol % of the glass ceramic.

Characterizing for the invention is also the fact that the lithium aluminum silicate crystals/crystallites are grown on the lithium disilicate crystals, in particular on their front faces, with the lithium disilicate crystals having a rod shape or plate shape.

In particular according to the invention the length LS of the spodumene crystals/crystallites is in the range $1\ nm \leq LS \leq 500\ nm$, in particular $1\ nm \leq LS \leq 300\ nm$, especially $1\ nm \leq LS \leq 200\ nm$.

The length of the virgilite crystals should be in the range 0.2 μm to 20 μm, in particular 0.5 μm to 10 μm.

The invention is in particular characterized in that the lithium silicate glass ceramic has the following composition in wt %:
$SiO_2$ 54.0-62.0, preferably 57.0-62.0,
$P_2O_5$ 5.0-6.0
$Al_2O_3$ 1.5-3.5
$Li_2O$ 13.0-16.0
$K_2O$ 0.6-1.8
$ZrO_2$ 8.0-11.5
$B_2O_3$ 0-6.0
$Na_2O$ 0-1.9
color pigment/s 0-8.0
such as MnO, $Fe_2O_3$,
$Tb_2O_3$, $Er_2O_3$, $Pr_2O_3$, $CeO_2$, $Y_2O_3$,
$V_2O_3$.

Preferably the invention is characterized in that the lithium silicate glass ceramic has the following composition in wt %:
$SiO_2$ 57.0 to 60.0
$P_2O_5$ 5.2 to 5.6

$Al_2O_3$ 2.6 to 3.2
$Li_2O$ 13.5 to 15.0
$K_2O$ 0.8 to 1.4
$ZrO_2$ 9.0 to 11.0
$B_2O_3$ 0 to 5.0
$Na_2O$ 0 to 1.5
color pigment/s 2.0 to 7.0
including optionally $CeO_2$.

It is especially preferred for the lithium silicate glass ceramic to contain or comprise the following components in wt %:
$SiO_2$ 58
$P_2O_5$ 5
$Al_2O_3$ 3
$Li_2O$ 15
$K_2O$ 1
$ZrO_2$ 10.0
color pigment/s 4
such as $MnO$, $Fe_2O_3$, $Tb_2O_3$, $Er_2O_3$, $Pr_2O_3$, $Y_2O_3$, $V_2O_3$. additives such as $B_2O_3$, $CeO_2$, $Na_2O$ especially degassing agents, such as $CeO_2$ and/or network builders, such as $B_2O_3$.

It was surprisingly found that the strength was substantially increased as a result of the crystals/crystallites of lithium aluminum silicate contained in the lithium silicate glass ceramic. Three-point bending strength measurements in accordance with ISO 6872 consequently showed that the strength of the lithium silicate glass ceramic according to the invention, which additionally contains spodumene as the crystal phase, is increased by 35% to 140% relative to a corresponding glass ceramic without this crystal phase, depending on whether a block of lithium silicate glass ceramic was used as the starting material for production of a molded body through material-removing working such as milling or a pressed blank (press pellet) of lithium silicate glass ceramic was used.

A method to produce a lithium silicate glass ceramic intended for a dental form body comprises at least the following steps:
  Melting of the starting components containing at least $SiO_2$, $Al_2O_3$, $Li_2O$, $K_2O$, at least one nucleating agent such as $P_2O_5$, at least one stabilizer such as $ZrO_2$, as well as where necessary at least one color-imparting metal oxide,
  Filling of homogenized melt into containers,
  Cooling of the melt to room temperature,
  First heat treatment of the mold parts removed from the containers to form at least one first crystal phase,
  Cooling of the mold parts,
  Formation of a further crystal phase in the form of lithium aluminum silicate through a second heat treatment and
  Cooling of the mold parts to room temperature.

During the first heat treatment lithium disilicate crystals are formed as main crystal phase, especially lithium disilicate crystals and lithium phosphate crystals are exclusively formed.

During the second or further heat treatment lithium aluminum silicate crystals are formed.

Thereby prior to the second heat treatment, but after the first crystal phase has been formed, a pressing of the mold parts may be carried out to derive a dental restoration such as an inlay, onlay, part-crown, crown, bridge or abutment.

As an alternative, there is the possibility of producing molded bodies from the molded parts (e.g. a blank or block) through material removing procedures such as milling, in particular manufacturing an inlay, onlay, crown, part-crown, bridge or abutment.

The invention in particular provides for the second or further heat treatment to form the lithium aluminum silicate crystal phase to be carried out at a temperature TW2 between 720° C. and 780° C., in particular between 750° C. and 780° C., wherein the molded part is maintained at this temperature for a period of time tW2, wherein preferably 1 minute≤tW2≤60 minutes, in particular 1 minute≤tW2≤5 minutes, especially preferred 60 seconds≤t≤150 seconds. The molding is thereby heated from room temperature at a heating rate of between 40° C./minute and 100° C./minute until the desired holding temperature is reached. The holding period is followed by the usual cooling.

In particular in the first heat treatment, which can be carried out in a number of stages, in particular three stages, lithium disilicate and lithium phosphate are exclusively formed as crystal phases.

The invention in particular provides, when the molded parts are being pressed, for them to be held over a period tP where 20 minutes≤tP≤40 minutes, in particular where tP is approximately 30 minutes, at a temperature TP where 820° C.≤TP≤900° C., in particular where TP is approximately 860° C., and then pressed. Cooling of the pressed molded parts, i.e., molded bodies, in particular dental reconstructions, is then to be carried out in that furnace in which the molded part or molded parts, in particular dental restorations, are pressed in the cavity of the embedding mass, which I determines the geometry of the molded body.

The invention is characterized by the use of a lithium silicate glass ceramic which contains as the crystal phase lithium aluminum silicate with a percentage by volume of more than 0 vol % to 10 vol %, in particular more than 0 vol % to 5 vol %, especially preferred more than 0 vol % to 2 vol %, more especially preferred more than 0 vol % to 1 vol %, for the production of a dental molded body.

Further details, advantages and features of the invention are derived not just from the claims, the features to be derived therefrom—alone and/or in combination—but also from the following description of preferred embodiment examples, as well as the enclosed drawings.

DETAILED DESCRIPTION OF THE INVENTION

Figure 1:
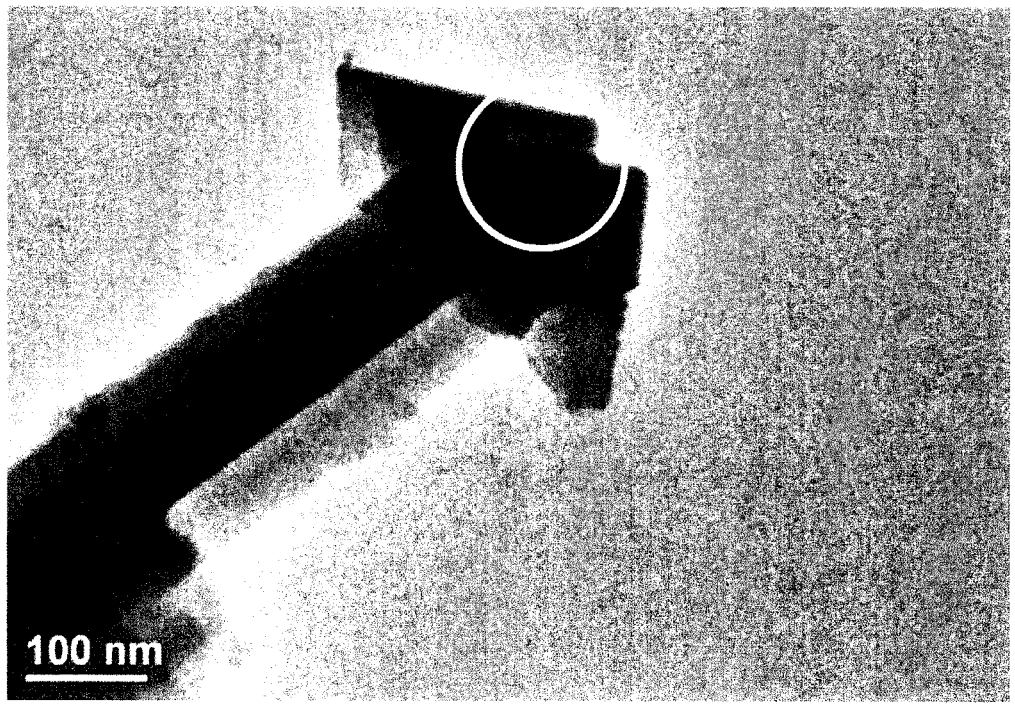
FIG. 1 shows a electron microscope photograph of a disilicate crystal with grown spodumene crystallite.

In a first test molded parts in the form of pellets were fabricated and then pressed in a so-called muffle system (DentsplySirona Press muffel and ProFire Press furnace) to obtain a dental restoration in the form of a bridge.

To produce the pellets the raw materials were first melted for a period of 2.25 hours at a temperature of 1540° C. The raw materials had the following composition in percentage by weight:
$SiO_2$ 58
$P_2O_5$ 5
$Al_2O_3$ 3

Li$_2$O 15
K$_2$O 1
ZrO$_2$ 10
color pigments 4
degassing agents, network builder 4.

The melt was then filled into containers, with the filling temperature of the melt 1360° C. The temperature in the containers was approximately in the range 800° C. to 1250° C. The melt was then cooled in the containers to a temperature between 300° C. and 500° C. The temperature was then allowed to drop slowly to room temperature over a period of 2 hours.

This was followed by a 3-stage heat treatment as a first heat treatment to form crystal phases. In a first crystallization step the pellets were maintained at a temperature of 530° C. for 30 minutes. In a second step they were heated at 670° C. for almost 120 minutes. In a third step they were maintained at 800° C. for 30 minutes. They were then cooled to room temperature. The pellets were found to contain exclusively lithium disilicate and lithium phosphate as crystal phases.

The pellets (press pellets) were held in a muffle system (Dentsply Sirona Pressmuffel and ProFire Press) at a temperature TP of 860° C. for a period tP of 30 minutes and then pressed. After cooling of the molded body formed in the cavity of the embedding mass, which was a bending rod according to ISO 6872, the strength was measured. Measurements were performed in accordance with ISO 6872 and yielded a mean strength of 398 MPa.

A further (second) heat treatment was then carried out according to the teaching of the invention. For this purpose the mold bodies were heated to 760° C. at a heating rate of 55° C./minute and were then held at 760° C. for 2 minutes. During this second treatment lithium aluminum silicate crystals are formed. The mold bodies were then cooled under standard conditions in a Multimat dental furnace (manufacturer: Dentsply Sirona).

Three-point measurements in accordance with ISO 6872 yielded a strength of 591 MPa.

In further tests the second heat treatment was carried out in such a way that the holding temperature was 770° C. and the holding time was 1.5 minutes. The same increase in strength was achieved.

In a second test run moldings were produced with lithium disilicate and lithium phosphate as the crystal phases as described above, with the composition of the starting materials in percentage by weight as follows:
SiO$_2$ 58
P$_2$O$_5$ 5
Al$_2$O$_3$ 3
Li$_2$O 15
K$_2$O 1
ZrO$_2$ 10.0
color pigments 4
degassing agents, network builders 4

Rods with the dimensions length 15 mm, width 4.1 mm and height 1.2 mm were derived from the moldings after crystallization through grinding. Three-point bending strength measurements in accordance with ISO 6872 yielded a strength value of 270 MPa.

Corresponding rods were then subjected to the further or second heat treatment according to the invention, and were heated to 760° C. at a heating rate of 55° C./minute. The rods were held at this temperature for 2 minutes. They were then cooled under standard conditions in a Multimat MT dental furnace (manufacturer: Dentsply Sirona). The strength upon measurement in accordance with ISO 6872 was 598 MPa.

X-ray diffraction examination with a transmission electron microscope (TEM) revealed that spodumene crystals had grown on the ends of the lithium disilicate crystals. Virgilite crystals were also seen in some samples.

FIG. 1 is an electron microscope photograph of a lithium disilicate crystal with a spodumene crystallite which is marked by a surrounding circle.

Figure 2:
FIG. 2 shows a x-ray diffraction photograph of the spodumene crystallite of FIG. 1.

FIG. 2 is a x-ray diffraction photograph of the spodumene crystallite of FIG. 1. This makes spodumene identifiable.

Figure 3:
FIG. 3 shows a electron microscope photograph of disilicate crystals.

FIG. 3 is an electron microscope photograph of lithium silicate glass ceramic. The rod-like or plate-like disilicate crystals are visible.

Figure 4:
FIG. 4 shows a electron microscope photograph of disilicate crystals with spodumene crystals.
Figure 5:
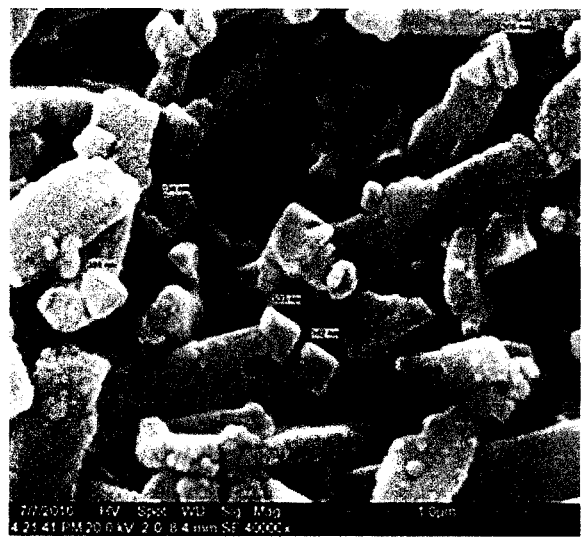
FIG. 5 shows a further electrone microscope photograph of disilicate crystals with spodumene crystals.

FIGS. 4 and 5 are electron microscope photographs of silicate glass ceramic which was subjected to heat treatment according to the invention. In FIG. 4, the further or second heat treatment was carried out at a temperature of 760° C. at a holding time of 2 min., and in FIG. 5 at 760° C. at a holding time of 60 min. The spodumene crystallites grown are visible at the faces of the disilicate crystals.

The invention claimed is:
1. A method for the production of a lithium silicate glass ceramic intended for a dental molded body, comprising the following steps:
   a) melting of the starting components containing at least SiO$_2$, P$_2$O$_5$, Al$_2$O$_3$, Li$_2$O, K$_2$O, ZrO$_2$,
   b) filling of the melt into containers,
   c) cooling of the melt to room temperature,
   d) performance of a crystallization in the melt that has solidified to molded parts by means of a first heat treatment,
   e) cooling to room temperature,
   f) performance of a second heat treatment, wherein the molded parts are heated to a temperature TW2 between 720° C. and 780° C. and are held at this temperature for a time period tW2,
   g) cooling of the molded parts to room temperature;
   wherein the first heat treatment is carried out in three steps, wherein in a first step the molded part is maintained for a time t1 where 1 minute≤t1≤60 minutes at a temperature T1 where 250° C.≤T1≤600° C.,
   wherein in the second step, the molded part is maintained for a time t2 where 1 minute≤t2≤150 minutes at a temperature T2 where 600° C.≤T2≤700° C., and
   wherein in the third step the molded part is held for a time t3 where 10 minutes≤t3≤60 minutes at a temperature T3 where 700° C.≤T3≤850° C.

2. The method according to claim 1, wherein in method step d) lithium disilicate and lithium phosphate are exclusively formed.

3. The method according to claim 1, wherein crystallization of lithium aluminum silicate crystals occurs during the second heat treatment, which is carried out for the time tW2 with 1 minute≤tW2≤60 minutes.

4. The method according to claim 1, wherein following method step e) and before method step f) the molded part for production of a molded body is pressed or the molded part for production of a molded body is worked in a material-removing manner.

5. The method according to claim 1, wherein the second heat treatment for crystallization of lithium aluminum silicate crystals is carried out at the temperature TW2 where 750° C.≤tW2≤780° C. for the time tW2 where 1 minute≤tW2≤4 minutes.

6. A method for the production of a lithium silicate glass ceramic intended for a dental molded body, comprising the following steps:

a) melting of the starting components containing at least $SiO_2$, $P_2O_5$, $Al_2O_3$, $Li_2O$, $K_2O$, $ZrO_2$,
b) filling of the melt into containers,
c) cooling of the melt to room temperature,
d) performance of a crystallization in the melt that has solidified to molded parts by means of a first heat treatment,
e) cooling to room temperature,
f) performance of a second heat treatment, wherein the molded parts are heated to a temperature TW2 between 720° C. and 780° C. and are held at this temperature for a time period tW2,
cooling of the molded parts to room temperature;
    wherein for pressing the molded part it is held at a temperature TP where 730° C.≤TP≤900° C. for a time tP where tP 10 minutes≤tP≤50 minutes, and then pressed.

7. The method according to claim 6, wherein in method step d) lithium disilicate and lithium phosphate are exclusively formed.

8. The method according to claim 6, wherein crystallization of lithium aluminum silicate crystals occurs during the second heat treatment, which is carried out for the time tW2 with 1 minute≤tW2≤60 minutes.

9. The method according to claim 6, wherein following method step e) and before method step f) the molded part for production of a molded body is pressed or the molded part for production of a molded body is worked in a material-removing manner.

10. The method according to claim 6, wherein the second heat treatment for crystallization of lithium aluminum silicate crystals is carried out at the temperature TW2 where 750° C.≤tW2≤780° C. for the time tW2 where 1 minute≤tW2≤4 minutes.

11. A use of a lithium silicate glass ceramic, which comprises as the crystal phase lithium aluminum silicate, at least in form of spodumene, with a percentage by volume of more than 0 vol % to 10 vol % of lithium silicate glass ceramic, for the production of a dental molded body; wherein the lithium silicate glass ceramic includes sogdianite.

12. The use according to claim 11, wherein the lithium silicate glass ceramic includes virgilite.

* * * * *